(12) United States Patent
Bogaerts et al.

(10) Patent No.: US 11,298,277 B2
(45) Date of Patent: Apr. 12, 2022

(54) ADHESIVE TAPE ASSEMBLIES

(71) Applicant: Avery Dennison Corporation, Glendale, CA (US)

(72) Inventors: Bert Bogaerts, Boechout (BE); Johan Van Steen, Ravels (BE); Anne Verhaert, Turnhout (BE)

(73) Assignee: Avery Dennison Corporation, Glendale, CA (US)

( * ) Notice: Subject to any disclaimer, the term of this patent is extended or adjusted under 35 U.S.C. 154(b) by 631 days.

(21) Appl. No.: 16/090,958

(22) PCT Filed: Apr. 12, 2017

(86) PCT No.: PCT/US2017/027136
§ 371 (c)(1),
(2) Date: Oct. 3, 2018

(87) PCT Pub. No.: WO2017/180702
PCT Pub. Date: Oct. 19, 2017

(65) Prior Publication Data
US 2019/0117480 A1    Apr. 25, 2019

Related U.S. Application Data

(60) Provisional application No. 62/321,821, filed on Apr. 13, 2016.

(51) Int. Cl.
*A61F 13/15* (2006.01)
*A61F 13/58* (2006.01)
(Continued)

(52) U.S. Cl.
CPC .......... *A61F 13/58* (2013.01); *A61F 13/5512* (2013.01); *A61F 13/565* (2013.01); *A61F 13/5622* (2013.01)

(58) Field of Classification Search
CPC .. A61F 13/58; A61F 13/5512; A61F 13/5622; A61F 13/565
(Continued)

(56) References Cited

U.S. PATENT DOCUMENTS 2,162,108 A    6/1939 Newman
4,237,890 A  * 12/1980 Laplanche .............. A61F 13/58
                                                        604/390
(Continued)

FOREIGN PATENT DOCUMENTS

EP    0861642    9/1998
JP    5-117607   5/1993
(Continued)

OTHER PUBLICATIONS

International Search Report and Written Opinion issued in corresponding IA No. PCT/US2017/027136 dated Jun. 20, 2017.
(Continued)

*Primary Examiner* — Jacqueline F Stephens
(74) *Attorney, Agent, or Firm* — Avery Dennison Corporation

(57) ABSTRACT

Various fastening tape closure assemblies are described. The closure tapes are useful in the manufacture of disposable articles, and particularly disposable diapers. The closure tapes generally include a fastening component, an extension component, and a bonding component. The tape systems provide a new folding configuration and reduced adhesive along a face of the extension component. Also described are disposable articles utilizing the tape closure assemblies.

18 Claims, 5 Drawing Sheets

(51) Int. Cl.
*A61F 13/551* (2006.01)
*A61F 13/56* (2006.01)

(58) Field of Classification Search
USPC .................. 604/386, 389, 390, 391, 394
See application file for complete search history.

(56) References Cited

U.S. PATENT DOCUMENTS

| | | | |
|---|---|---|---|
| 4,778,701 A * | 10/1988 | Pape | A61F 13/58 |
| | | | 428/41.8 |
| 4,801,480 A * | 1/1989 | Panza | A61F 13/58 |
| | | | 428/41.9 |
| 5,182,156 A | 1/1993 | Pape et al. | |
| 5,549,592 A * | 8/1996 | Fries | A61F 13/58 |
| | | | 604/389 |
| 6,656,171 B1 | 12/2003 | Matsuda et al. | |
| 7,291,371 B2 | 11/2007 | Verhaert | |
| 8,080,198 B2 | 12/2011 | Verhaert et al. | |
| 2004/0170794 A1 | 9/2004 | Verhaert | |
| 2009/0098023 A1 | 1/2009 | Verhaert et al. | |
| 2009/0292270 A1 * | 11/2009 | Showole | C09J 7/38 |
| | | | 604/390 |
| 2013/0184671 A1 | 7/2013 | Bogaerts | |
| 2014/0010984 A1 | 1/2014 | Bogaerts | |
| 2014/0088543 A1 | 3/2014 | Bogaerts et al. | |

FOREIGN PATENT DOCUMENTS

| | | |
|---|---|---|
| JP | 8-239635 | 9/1996 |
| JP | 2006-045417 | 2/2006 |
| JP | 2010-529887 | 9/2010 |
| WO | 2008/156931 | 12/2008 |

OTHER PUBLICATIONS

International Preliminary Report on Patentability dated Oct. 16, 2018 issued in corresponding IA No. PCT/US2017/027136 filed Apr. 12, 2017.

* cited by examiner

ADHESIVE TAPE ASSEMBLIES

CROSS REFERENCES TO RELATED APPLICATIONS

The present application is a 371 of International Application No. PCT/US17/27136, which was published in English on Oct. 19, 2017, and claims the benefit of U.S. Provisional Patent Application No. 62/321,821 filed Apr. 13, 2016, both of which are incorporated herein by reference in their entireties.

FIELD

The present subject matter relates to a closure tape assembly. Closure tapes are useful in disposable articles, and particularly disposable diapers.

BACKGROUND

Training pants or "pant diapers" are often used for young children during potty training. Pant diapers also have application in the adult incontinence market. Pant diapers are typically thinner than diapers and are designed to include certain aspects of both diapers and underwear.

Pant diapers are available in reusable form which must be washed between uses, or one-time disposable forms. Disposable forms include one or more adhesive tape assemblies which are typically used to maintain a used diaper in a "rolled-up" form after use to facilitate handling and disposal.

Although currently known tape assemblies used in disposable diapers are satisfactory in many respects, in many instances during disposal one or more regions of adhesive in the tape assemblies are exposed and can inadvertently "stick" to waste containers or the user attempting disposal. For at least this reason, a new closure tape assembly is needed which overcomes these concerns.

SUMMARY

The difficulties and drawbacks associated with previous approaches are addressed in the present subject matter as follows.

In one aspect, the present subject matter provides a fastener tape assembly comprising a fastening component defining a folded edge. The tape assembly also comprises a bonding component defining a first face for affixment to a diaper or substrate and an oppositely directed second face. The tape assembly additionally comprises an extension component having an edge received within the folded edge of the fastening component and generally disposed between the fastening component and the bonding component. The folded edge of the fastening component and the edge of the extension component extend beyond an edge of the bonding component.

In another aspect, the present subject matter provides a fastener tape assembly comprising a fastening component defining a folded edge. The tape assembly also comprises a bonding component defining a first face for affixment to a diaper or substrate and an oppositely directed second face. The tape assembly also comprises an extension component having an edge received within the folded edge of the fastening component and generally disposed between the fastening component and the bonding component. The extension component defines a face directed toward the bonding component and the face includes at least one of (i) a region of patterned adhesive, and (ii) an adhesive-free region.

In yet another aspect, the present subject matter provides a fastener tape assembly comprising a fastening component defining a first edge and a second edge, referred to as the distal edge and a folded edge. The fastener tape assembly also comprises a bonding component defining a first face for affixment to a diaper or substrate and an oppositely directed second face. The fastener tape assembly also comprises a first folded edge component having a first leg and a second leg. And, the fastener tape assembly additionally comprises an extension component having an edge received between the first leg and the second leg of the first folded edge component. The extension component is generally disposed between the fastening component and the bonding component. The first folded edge component and the edge of the extension component extend beyond an edge of the bonding component.

In another aspect, the present subject matter provides an article including a fastener tape assembly. The fastener tape assembly includes a fastening component defining a folded edge. The fastener tape assembly also includes a bonding component defining a first face affixed to the article and an oppositely directed second face. The fastener tape assembly additionally includes an extension component having an edge received within the folded edge of the fastening component and generally disposed between the fastening component and the bonding component. The folded edge of the fastening component and the edge of the extension component extend beyond an edge of the bonding component.

In still another aspect, the present subject matter provides an article including a fastener tape assembly. The fastener tape assembly includes a fastening component defining a folded edge. The fastener tape assembly also includes a bonding component defining a first face affixed to the article and an oppositely directed second face. And, the fastener tape assembly additionally includes an extension component having an edge received within the folded edge of the fastening component and generally disposed between the fastening component and the bonding component. The extension component defines a face directed toward the bonding component and the face includes at least one of (i) a region of patterned adhesive, and (ii) an adhesive-free region.

In yet another aspect, the present subject matter provides an article including a fastener tape assembly. The fastener tape assembly includes a fastening component defining a first edge and a second edge, referred to as the distal edge and a folded edge. The fastener tape assembly also comprises a bonding component defining a first face for affixment to the article and an oppositely directed second face. The fastener tape assembly additionally comprises a first folded edge component having a first leg and a second leg. The fastener tape component also comprises an extension component having an edge received between the first leg and the second leg of the first folded edge component. The extension component is generally disposed between the fastening component and the bonding component. The first folded edge component and the edge of the extension component extend beyond an edge of the bonding component.

As will be realized, the subject matter described herein is capable of other and different embodiments and its several details are capable of modifications in various respects, all without departing from the claimed subject matter. Accordingly, the drawings and description are to be regarded as illustrative and not restrictive.

DETAILED DESCRIPTION OF THE EMBODIMENTS

The present subject matter fastener tape assemblies and systems provide improved disposability. In one embodiment, opening of the tape assembly is improved by changing a folding configuration and manner by which the assembly is folded. This configuration and method of folding significantly reduce and can eliminate the potential for tape delamination from a diaper upon opening.

In another embodiment, the fastener tape assemblies utilize an adhesive pattern or adhesive-free region along a region of an extension component of the fastener tape assembly. As a result of the use of such region of patterned adhesive or adhesive-free region, the potential for inadvertent adhesive "sticking" of that component to waste containers such as bags or bins, is significantly reduced and in certain instances is eliminated.

New Folding Configuration

Certain fastener tape systems known in the art and particularly those known as "Z-fold" tapes are susceptible to delamination from an underlying diaper or other substrate upon opening of the tape assembly. This is largely due to an outer fastening component of the tape assembly adhering to a bonding component which is affixed, adhered or otherwise bonded to the diaper.

Figure 1:
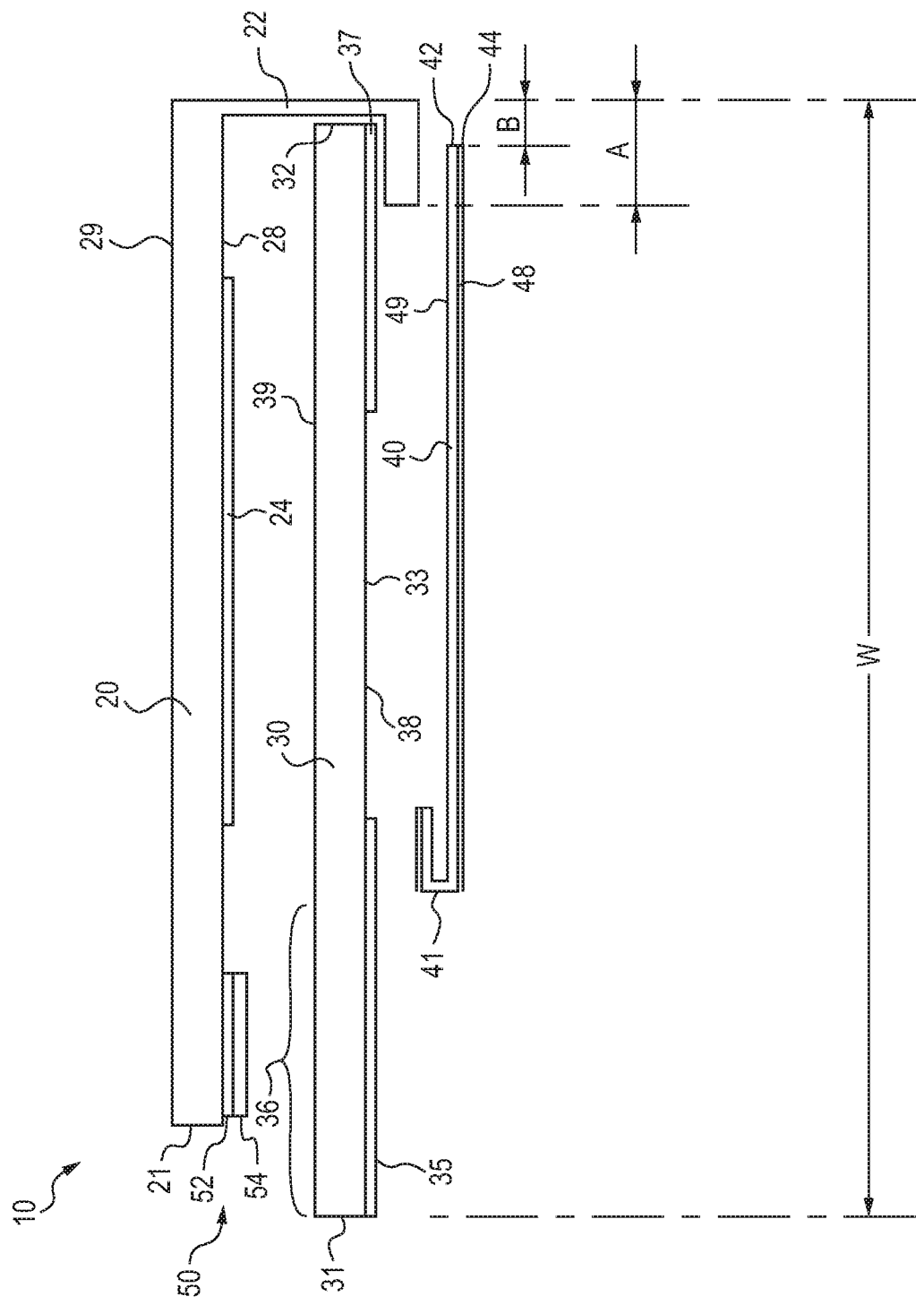
FIG. 1 is a schematic illustration of a fastener tape assembly in accordance with the present subject matter.

In accordance with an embodiment of the present subject matter, a new folding configuration is provided for the fastening component and an extension component of the tape assembly and their relation with a bonding component. Referring to FIG. 1, a new folding configuration is shown for an embodiment of a fastener tape assembly in accordance with the present subject matter. The fastener tape assembly 10 depicted in FIG. 1 includes a fastening component designated as 20, an extension component designated as 30, and a bonding component designated as 40. The new folding configuration includes a folded edge 22 in the fastening component 20 that: (i) receives a corresponding edge 32 of the extension component 30, and (ii) is offset from a corresponding edge 42 of the bonding component 40 of the tape assembly. Thus, as compared to certain other known tape assemblies, the folded edge 42 of the bonding component 40 need not extend to, or be co-extensive with, the folded edge 22 of the fastening component 20. Referring to FIG. 1, this feature is illustrated as the dimensional offset B that extends beyond the folded edge 42 of the bonding component 40. The fact that the edge 42 of the bonding component 40 is not extending beyond one or both of the corresponding edges (32 edge, 22 folded edge) of the extension component 30 and/or the fastening component 20, is a benefit in many applications of the tape assemblies. This is because thinner materials can then be used for the bonding component 40 since stacking rolls of the tape assemblies in a pallet for example, will not affect the roll quality. If a relatively thin material is used for the bonding component in a conventional fastener tape assembly and in a configuration in which the bonding component extends beyond the edge(s) of the fastening component and/or the extension component, that thin material will fold over resulting in a loss of bonding.

As noted herein, in many embodiments relatively thin materials can be used for one or more or all of the fastening component, extension component, and bonding component. Typically, the fastening component has a thickness within a range of from about 30 µm to about 120 µm and particularly from about 50 µm to about 90 µm. The extension component has a thickness within a range of from about 30 µm to about 120 µm, and particularly from about 50 µm to about 90 µm. The bonding component has a thickness within a range of from about 15 µm to about 120 µm, and particularly from about 20 µm to about 50 µm. The total thickness of the fastener tape assembly is typically within a range of from about 200 µm to about 600 µm, and in many embodiments from about 250 µm to about 500 µm.

As noted, use of this new folding configuration can in certain applications enable the use of thinner materials for the tape assembly and its components. This is because rolls of fastener tape incorporating the new folding configuration will no longer be carried on a portion of the bonding component otherwise extending to the fold location. Instead, such rolls will be carried on a significantly more stable portion of the tape assembly.

Utilizing this new folding configuration also promotes dimensional certainty as to the location at which the fastener tape assembly will open.

Region of Patterned Adhesive or Adhesive-Free Region on Extension Component

Another embodiment of the fastener tape assemblies of the present subject matter relates to improving disposability. Referring to FIG. 1, a face 38 of the extension component 30 of the fastener tape assembly 10 that is directed toward the bonding component 40, can include a region of patterned adhesive 35 and/or at least one adhesive-free region 33 that is free of adhesive or "adhesive-free." Thus, upon opening of the tape assembly 10 and use in a diaper, the noted face 38 of the extension component 30 which includes a reduced face area of adhesive due to the adhesive-free region 33 and/or the region of patterned adhesive 35, will not interfere or interfere significantly less as compared to conventional tape constructions, with disposal of the diaper. It will be understood that the present subject matter includes a wide array of embodiments and that the previously described folding configuration can be used with, or without, the adhesive aspects for the extension component.

Additional Aspects

It will be appreciated that the present subject matter includes fastener tape assemblies that include (i) the new folding configuration, (ii) region of patterned adhesive or adhesive-free region on the extension component, or both (i) and (ii).

Referring to FIG. 1, it will also be understood that the attachment of the bonding component 40 to the extension component 30 of the fastener tape systems of the present subject matter can be in a variety of different forms including, but not limited to, a U-bond or utilize a U-bond strip, or in the form of a Y-bond as described in U.S. Pat. No. 6,656,171.

FIG. 1 illustrates additional features and aspects of the present subject matter fastener tape assemblies and systems of the present subject matter. Referring further to the fastener tape assembly 10 depicted in FIG. 1, it will be noted that in many embodiments of the present matter, a typical dimension for the "foldover," shown in the figures as "A" is within a range of from 4 to 10 mm, and more particularly from 4 to 6 mm, with 5 mm being useful for many applications. A typical total tape assembly width shown as "W" is from about 50 to 80 mm, with total widths of about 70.3 mm, about 69 mm, and about 62 mm being useful for certain applications. A significant aspect of the new folding configuration is that the difference between the foldover dimension A and the extent of dimensional offset B is sufficient in order to avoid delamination of the bonding component from the diaper. In many embodiments, this difference, i.e., A-B, is at least about 2 mm and in certain applications is at least 3 mm.

In another aspect of the present subject matter, a bond or affixment between the fastening component 20 and the extension component 30 is provided by a folded edge 22 of the fastening component 20 into which a corresponding edge 32 of the extension component 30 is inserted or otherwise disposed. This aspect is in contrast to a prior art configuration in which a folded edge region is provided in a middle component corresponding to the extension component of the present subject matter tape assemblies, and a top component corresponding to the fastening component of the present subject matter is merely positioned on top or otherwise along the folded edge region of the middle component. That is, in the known prior art, the top component is not inserted within the folded edge region of the middle component.

Yet another aspect of the present subject matter tape assemblies relates to provision of a "leg" portion of the extension component. Referring to FIG. 1, this leg portion 36 of the extension component 30 is the portion of the extension component 30 that extends beyond a U-bond or Y-bond edge 41 of the bonding component 40. However, it will be understood that the present subject matter includes tape assemblies free of this leg portion 36. In addition, it will be appreciated that the present subject matter includes tape assemblies that include additional components such as for example an extra film, strip or like component that is folded in a U-bond configuration to provide a bond between the extension component 30 and the bonding component 40. Moreover, one or more additional components such as coated tape components could be used.

Additional details of the fastener tape assembly 10 shown in FIG. 1 are as follows. The fastening component 20 defines a first face 28 and a second face 29 oppositely directed from the first face 28. The fastening component 20 also defines a distal edge 21 generally opposite from the folded edge 22. An adhesive region 24 extends along at least a portion of the first face 28 of the fastening component 20. In many versions of the fastener tape assemblies such as fastener tape assembly 10, a fingerlift 50 is provided proximate the distal edge 21 of the fastening component 20. The fingerlift 50 typically includes a tab 54 for gripping by a user and a region 52 of adhesive for securing the tab 54 to the fastening component 20 and typically to the first face 28.

The extension component 30 defines a face 39 oppositely directed from the face 38. And, the extension component 30 defines a distal end 31 opposite from the edge 32. In addition to the adhesive-free region 33 and the region of patterned adhesive 35, an adhesive region 37 is disposed along the face 38 of the extension component 30 for promoting and/or maintaining closure of the fastener tape assembly 10.

The bonding component 40 defines a first face 48 and a second face 49 generally oppositely directed from the first face 48. The bonding component 40 also includes a region 44 of adhesive disposed along at least a portion of the first face 48 of the bonding component 40. The region 44 of adhesive is for bonding or securing the fastener tape assembly 10 to a diaper or other substrate.

The present subject matter also provides variations of the fastener tape assembly 10 depicted in FIG. 1. For example, FIGS. 2, 3, 4, and 5 illustrate additional embodiments of fastener tape assemblies 210, 310, 410, and 510, respectively. In these figures, the fastener tape assemblies comprise the same or similar components as previously described in association with the fastener tape assembly 10 of FIG. 1, and thus use like numbering of such components. For example, the fastener tape assemblies 210, 310, 410, and 510 each comprise a fastening component 220, 320, 420, and 520, respectively, which is the same or similar as the fastening component 20 of assembly 10 shown in FIG. 1. However, the fastener tape assemblies 210, 310, 410, and 510 include several variations as compared to the fastener tape assembly 10 of FIG. 1 as follows.

Figure 2:
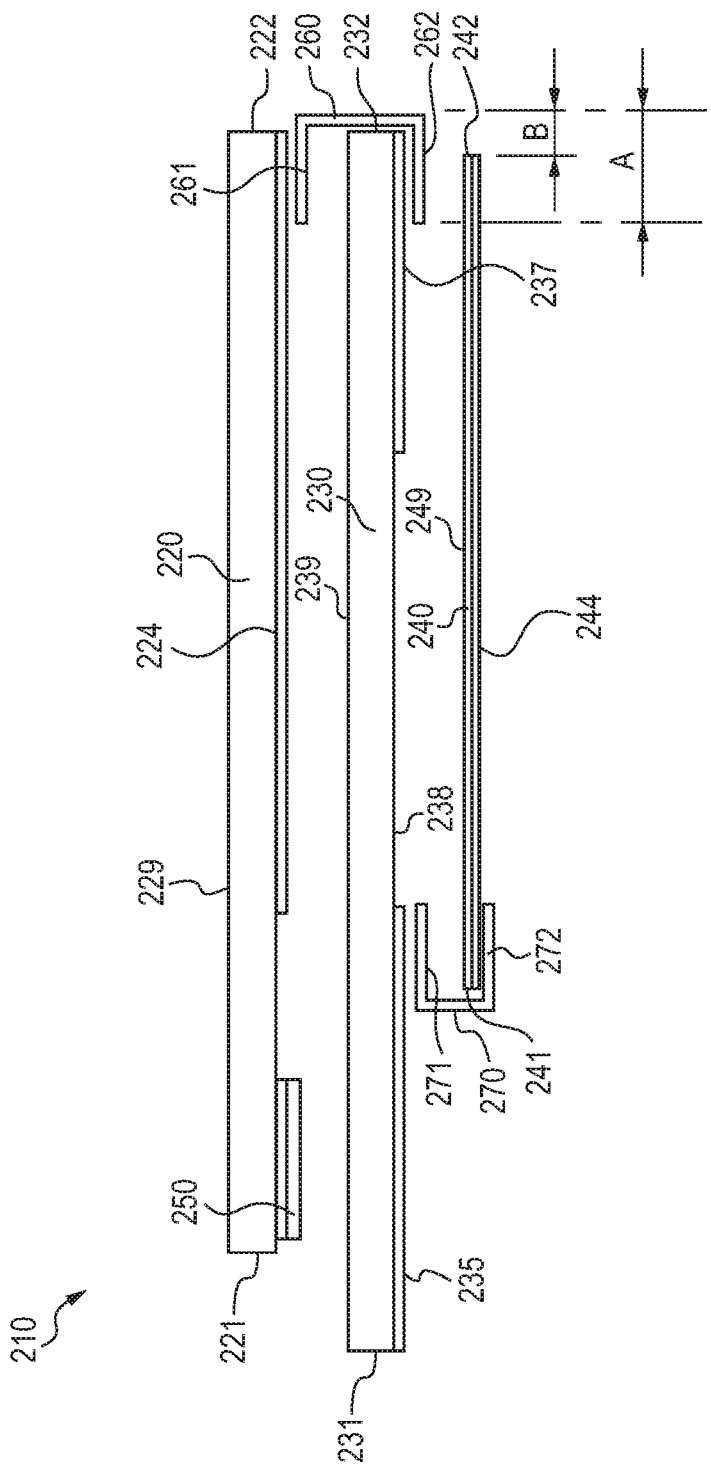
FIG. 2 is a schematic illustration of another fastener tape assembly in accordance with the present subject matter.

Fastener tape assembly 210 shown in FIG. 2 includes an ancillary affixment component or first "folded edge" 260. This component is typically separate from the fastening component 220. The first folded edge 260 includes two legs 261 and 262 between which is disposed an edge 232 of the extension component 230. Specifically, the leg 261 is positioned between the exposed face of the adhesive region 224 of the fastening component 220 and a face 239 of the extension component 230. The leg 262 is positioned between the adhesive region 237 of the extension component 230 and a face 249 of the bonding component 240. The folded edge 260 can be in the form of a U-bond or Y-bond as known in the art. Use of the folded edge component 260 enables avoidance of the folded edge 222 of the fastening component 220 of the fastener tape assembly 210.

The fastener tape assembly 210 shown in FIG. 2 also comprises another or second affixment component or "folded edge" 270. This component is typically separate from the bonding component 240. The folded edge 270 includes two legs 271 and 272 between which is disposed an edge 241 of the bonding component 240. The folded edge 270 can be in the form of a U-bond or Y-bond as known in the art. Specifically, the leg 271 is positioned between a face 238 of the extension component 230. The leg 272 is positioned to partially extend over the adhesive region 244 proximate the edge 241 of the bonding component 240. Use of the folded edge 270 enables avoidance of the folded edge 241 of the bonding component 240 of fastener tape assembly 210.

Figure 3:
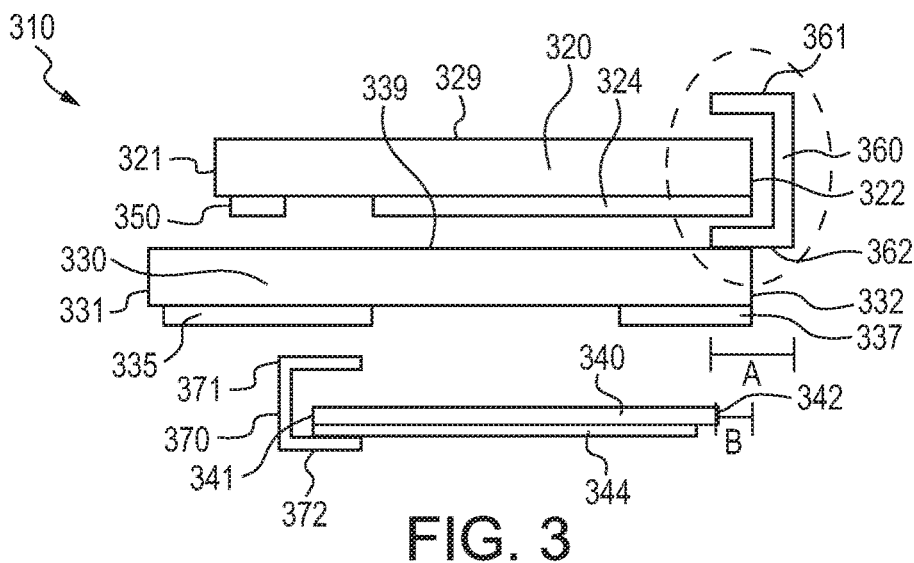
FIG. 3 is a schematic illustration of another fastener tape assembly in accordance with the present subject matter.

The fastener tape assembly 310 shown in FIG. 3 corresponds to the previously described fastener tape assembly 210 of FIG. 2 except for the position of the first folded edge. Instead of positioning the first folded edge proximate the edge of the extension component as in FIG. 2, in the assembly 310 of FIG. 3, the second folded edge shown as folded edge 360 is positioned to receive the edge 322 of the fastening component 320. In this embodiment, a leg 361 of the folded edge 360 extends partially over a face 329 of the fastening component 320, and a leg 362 is positioned between an adhesive region 324 of the fastening component 320 and a face 339 of the extension component 330. The assembly 310 also comprises a second folded edge 370 which is the same or similar to the second folded edge 270 described in assembly 210 of FIG. 2. The folded edge 360 and the second folded edge 370 may be in the form of a U-bond or Y-bond as known in the art.

Figure 4:
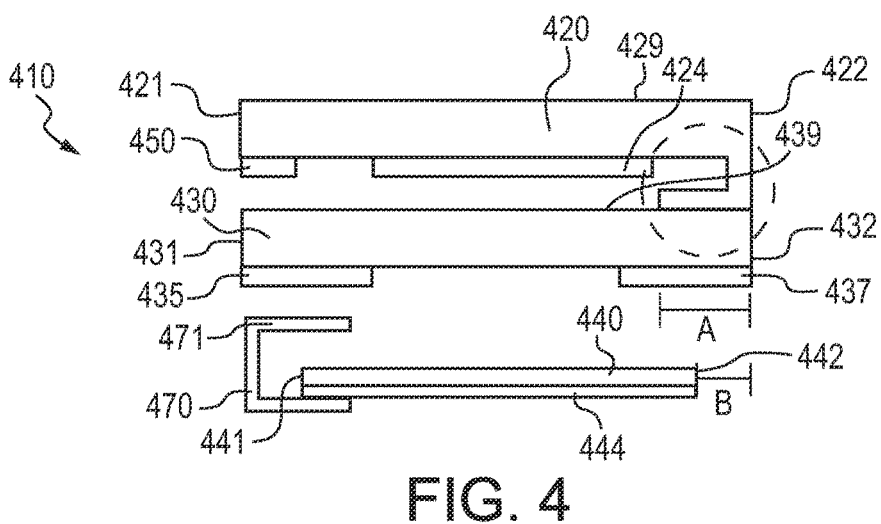
FIG. 4 is a schematic illustration of another fastener tape assembly in accordance with the present subject matter.

The fastener tape assembly 410 shown in FIG. 4 includes a folded edge 470 similar or the same as the folded edge 270 utilized in the fastener tape assembly 210 of FIG. 2. The folded edge 470 can be in the form of a U-bond or Y-bond as known in the art. However, the fastener tape assembly 410 is free of a separate folded edge corresponding to the folded edge 260 shown in FIG. 2. Instead, the fastener tape assembly 410 includes a configuration for the fastening component 420 similar to that of assembly 10 in FIG. 1, except that instead of positioning an edge 422 of the fastening component 420 between the extension component 430 and the bonding component 440; in fastener tape assembly 410, the edge 422 of the fastening component 420 is folded over itself and adhered or secured to a face 439 of the extension component 430 as shown in FIG. 4.

Figure 5:
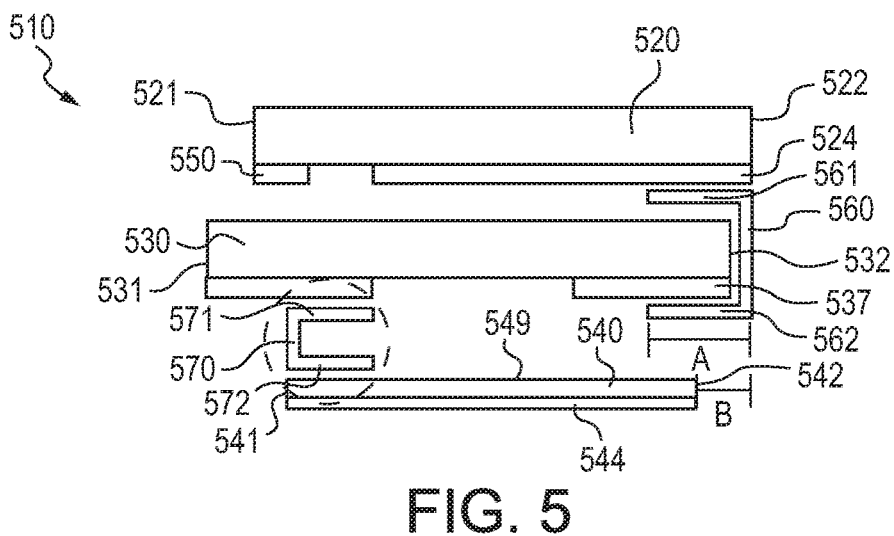
FIG. 5 is a schematic illustration of another fastener tape assembly in accordance with the present subject matter.

The assembly 510 shown in FIG. 5 is similar to the fastener tape assembly 210 of FIG. 2 except for the positioning of a leg 572 of the second folded edge 570. Specifically, as depicted in FIG. 5, a leg 572 of the second folded edge 570 is positioned between the extension component 530 and the bonding component 540, and specifically is directly adhered or affixed to a face 549 of the bonding component 540. The second folded edge 570 can be in the form of a U-bond or Y-bond as known in the art.

A wide array of adhesives can be used in the present subject matter tape assemblies. Typically, such adhesives are rubber-based styrene-isoprene-styrene (SIS) or styrene-butadiene-styrene (SBS)/styrene-butadiene (SB), or combinations thereof. Copolymers and/or derivatives of these and other adhesives could be utilized. The referenced figures illustrate typical regions of adhesive within the tape assemblies. In a particular embodiment, one or more regions of adhesive are provided in a region of the folded edge of the fastening component and/or along a corresponding edge of the extension component to thereby bond or affix the fastening component and the extension component together upon insertion or placement of that edge of the extension component within the folded edge of the fastening component.

Typical adhesive coatweights for all of the noted adhesive regions typically are from about 25 g/m² (gsm) to about 50 g/m² (gsm). However, the present subject matter includes coatweights less than or greater than these values.

A variety of polymeric films and materials can be used for one or more of the fastening component, extension component, and/or bonding component. Nonlimiting examples of polymeric films include polypropylene and/or polyethylene. Nonwoven materials and nonwoven laminates can also be used in the fastening tape assemblies. The noted Y and U bonds can be formed from appropriately configured polypropylene films and layer(s) of nonwoven materials.

Additional details regarding materials, thicknesses, manufacture, and uses of the present subject matter fastener tape assemblies are provided in one or more of the following patent documents assigned to Applicant: US 2014/0088543; U.S. Pat. Nos. 7,291,371; 8,080,198; US 2013/0184671; US 2014/0010984; US 2009/0008023; and US 2004/0170794. Articles The present subject matter also includes a wide array of articles that include the noted tape assemblies. In many embodiments, the articles are disposable, i.e., the articles are formed from materials that can be recycled and/or which are relatively inexpensive. Nonlimiting examples of such articles include diapers, training pants, adult diapers, and in particular pant diapers.

Figure 6:
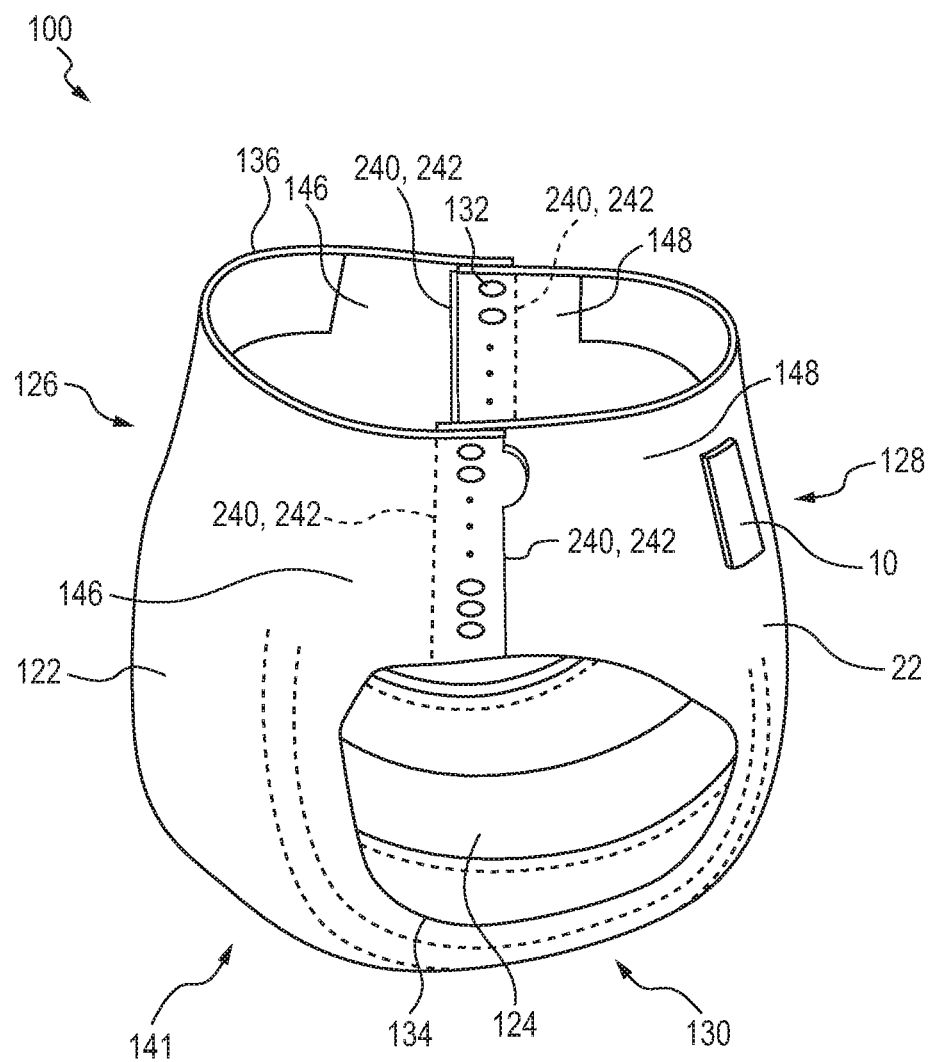
FIG. 6 is a perspective view of a disposable diaper having a fastener tape assembly in accordance with the present subject matter.

FIG. 6 illustrates an embodiment of a disposable article in accordance with the present subject matter. Referring to FIG. 6, the disposable article 100 has a front region 126, a back region 128, and a crotch region 130 between the front region 126 and the back region 128. A chassis 141 is provided in the front, back, and crotch regions 126, 128, and 130. The chassis 141 includes a liquid pervious topsheet 124, a liquid impervious backsheet 122 associated with the topsheet 124, and an absorbent core (not shown) disposed between the topsheet 124 and the backsheet 122.

The disposable article 100 further includes a pair of front ear panels 146 each extending laterally outward from the corresponding sides of the chassis 141 in the front region 126, and a pair of extensible back ear panels 148 each extending laterally outward from the corresponding sides of the chassis 141 in the back region 128. Each of the ear panels 146 and 148 has an outermost edge 240 which forms an outermost edge line 242. The disposable article 100 further includes seams 132 each joining the front and back ear panels 146 and 148 along the corresponding edge lines 242 to form the two leg openings 134 and the waist opening 136. The disposable article 100 includes a fastener tape assembly 10. Although fastener tape assembly 10 is shown, it will be understood that the subject matter includes other tape assemblies, such as the fastener tape assemblies 210, 310, 410, or 510.

Additional details of disposable articles, components and materials used in such, and their manufacture are described in U.S. Pat. No. 6,656,171.

Figure 7:
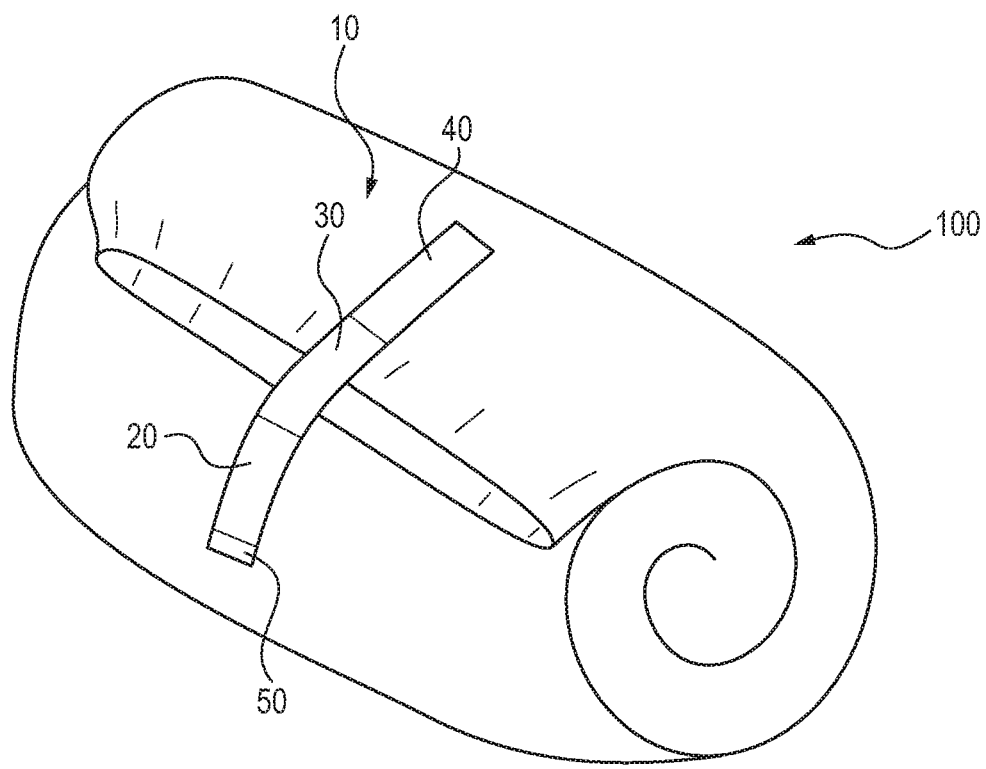
FIG. 7 is a perspective view of the diaper of FIG. 6 when the diaper is secured in a typical disposal configuration.

After the disposable article 100 has been soiled, the soiled disposable article 100 is torn open along the seams 132 to remove the soiled disposable article 100 from the wearer. Alternatively, if appropriate, the soiled disposable article 100 may be removed from the wearer by pulling down without tearing open the seams 132. The disposable article 100 is then folded or rolled up by keeping the crotch portion in the center so that the fastener assembly 10 is exposed along the outside of the rolled disposable article 100 for a convenient disposal as shown in FIG. 7, while containing the contents within the rolled disposable article 100.

Figure 8:
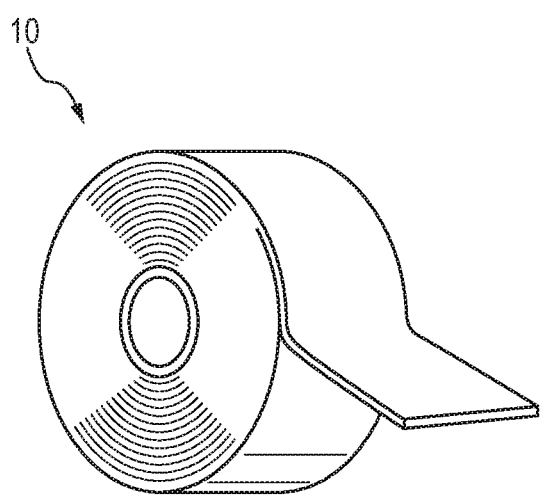
FIG. 8 is a perspective view of a closure tape roll in accordance with the present subject matter.

FIG. 8 is a perspective view of a roll of fastening tape assembly 10 in accordance with the present subject matter. The fastening tape assembly 10 can be provided in a roll form for use by a variety of manufacturers of disposable articles. Again, although the roll is shown for fastener tape assembly 10, it will be understood that any of the assemblies 210, 310, 410, or 510 can be provided in roll form.

Many other benefits will no doubt become apparent from future application and development of this technology.

All patents, applications, standards, and articles noted herein are hereby incorporated by reference in their entirety.

The present subject matter includes all operable combinations of features and aspects described herein. Thus, for example if one feature is described in association with an embodiment and another feature is described in association with another embodiment, it will be understood that the present subject matter includes embodiments having a combination of these features.

As described hereinabove, the present subject matter solves many problems associated with previous strategies, systems and/or devices. However, it will be appreciated that various changes in the details, materials and arrangements of components, which have been herein described and illustrated in order to explain the nature of the present subject matter, may be made by those skilled in the art without departing from the principle and scope of the claimed subject matter, as expressed in the appended claims.

What is claimed is:

1. A fastener tape assembly comprising:
   a fastening component defining a folded edge;
   a bonding component defining a first face for affixment to a diaper or substrate and an oppositely directed second face;
   an extension component having an edge received within the folded edge of the fastening component and generally disposed between the fastening component and the bonding component;
   wherein the folded edge of the fastening component and the edge of the extension component extend beyond an edge of the bonding component.

2. The fastener tape assembly of claim 1 wherein the extension component defines a face directed toward the bonding component and the face includes at least one of (i) a region of patterned adhesive, and (ii) an adhesive-free region.

3. The fastener tape assembly of claim 1 wherein adhesive is provided in a region of the folded edge to thereby bond the fastening component with the extension component.

4. The fastener tape assembly of claim 1 wherein adhesive is provided along at least a portion of the edge of the extension component that is received within the folded edge to thereby bond the fastening component with the extension component.

5. The fastener tape assembly of claim 1 wherein the fastener tape assembly is in a roll form.

6. The fastener tape assembly of claim 1, wherein at least one of the fastening component, the extension component, or the bonding component comprises a polymeric film selected from the group consisting of a polypropylene, a polyethylene and a combination thereof.

7. The fastener assembly according to claim 1, wherein an adhesive region extends along at least a portion of a first face of the fastening component.

8. A fastener tape assembly comprising:
   a fastening component defining a folded edge;
   a bonding component defining a first face for affixment to a diaper or substrate and an oppositely directed second face;
   an extension component having an edge received within the folded edge of the fastening component and generally disposed between the fastening component and the bonding component;
   wherein the extension component defines a face directed toward the bonding component and the face includes at least one of (i) a region of patterned adhesive, and (ii) an adhesive-free region.

9. The fastener tape assembly of claim 8 wherein the folded edge of the fastening component and the edge of the extension component extend beyond an edge of the bonding component.

10. The fastener tape assembly of claim 8 wherein the face of the extension component includes an adhesive-free region.

11. The fastener tape assembly of claim 8 wherein the face of the extension component includes the region of patterned adhesive.

12. The fastener tape assembly of claim 8 wherein the fastener tape assembly is in a roll form.

13. An article including a fastener tape assembly, the fastener tape assembly including:
    a fastening component defining a folded edge;
    a bonding component defining a first face affixed to the article and an oppositely directed second face;
    an extension component having an edge received within the folded edge of the fastening component and generally disposed between the fastening component and the bonding component;
    wherein the folded edge of the fastening component and the edge of the extension component extend beyond an edge of the bonding component.

14. The article of claim 13 wherein the article is a diaper.

15. The article of claim 14 wherein the diaper is a pant diaper.

16. An article including a fastener tape assembly, the fastener tape assembly including:
    a fastening component defining a folded edge;
    a bonding component defining a first face affixed to the article and an oppositely directed second face;
    an extension component having an edge received within the folded edge of the fastening component and generally disposed between the fastening component and the bonding component;
    wherein the extension component defines a face directed toward the bonding component and the face includes at least one of (i) a region of patterned adhesive, and (ii) an adhesive-free region.

17. The article of claim 16 wherein the article is a diaper.

18. The article of claim 17 wherein the diaper is a pant diaper.

* * * * *